United States Patent
Madhavan et al.

(10) Patent No.: US 10,905,882 B2
(45) Date of Patent: Feb. 2, 2021

(54) SYSTEMS AND METHODS FOR PREDICTING OPTIMAL DEEP BRAIN STIMULATION PARAMETERS

(71) Applicants: General Electric Company, Schenectady, NY (US); University Health Network, Toronto (CA)

(72) Inventors: Radhika Madhavan, Bangalore (IN); Alexandre Boutet, Toronto (CA); Suresh Joel, Bangalore (IN); Ileana Hancu, Poolesville, MD (US); Jeffrey Ashe, Gloversville, NY (US); Andres M. Lozano, Toronto (CA)

(73) Assignees: General Electric Company, Schenectady, NY (US); University Health Network, Toronto (CA)

( * ) Notice: Subject to any disclaimer, the term of this patent is extended or adjusted under 35 U.S.C. 154(b) by 115 days.

(21) Appl. No.: 16/253,406

(22) Filed: Jan. 22, 2019

(65) Prior Publication Data
US 2020/0230419 A1      Jul. 23, 2020

(51) Int. Cl.
*A61N 1/00* (2006.01)
*A61N 1/36* (2006.01)
(Continued)

(52) U.S. Cl.
CPC .......... *A61N 1/36135* (2013.01); *A61B 5/055* (2013.01); *A61B 5/7203* (2013.01);
(Continued)

(58) Field of Classification Search
CPC ............ A61N 1/36135; A61N 1/36025; A61N 1/36132–36139; A61N 1/0534;
(Continued)

(56) References Cited

U.S. PATENT DOCUMENTS

| 7,305,268 B2 | 12/2007 | Gliner et al. |
| 9,308,372 B2 | 4/2016 | Sparks et al. |

(Continued)

FOREIGN PATENT DOCUMENTS

| WO | 2013172981 A1 | 11/2013 |
| WO | 2017209673 A1 | 12/2017 |

(Continued)

OTHER PUBLICATIONS

Tang et al, A Probabilistic Atlas of Human Brainstem Pathways Based on Connectome Imaging Data, NeuroImage, vol. 169, Apr. 1, 2018, Amsterdam, NL, pp. 227-239.

*Primary Examiner* — Scott M. Getzow
(74) *Attorney, Agent, or Firm* — Ziolkowski Patent Solutions Group, SC; Jean K. Testa

(57) ABSTRACT

A system and method for optimizing parameters of a DBS pulse signal for treatment of a patient is provided. In predicting optimal DBS parameters, functional brain data is input into a predictor system, the functional brain data acquired responsive to a sweeping across a multi-dimensional parameter space of one or more DBS parameters. Statistical metrics of brain response are extracted from the functional brain data for one or more ROIs or voxels of the brain via the predictor system, and a DBS functional atlas is accessed, via the predictor system, that comprises disease-specific brain response maps derived from DBS treatment at optimal DBS parameter settings for a plurality of diseases or neurological conditions. One or more optimal DBS parameters are predicted for the patient based on the statistical metrics of brain response and the DBS functional atlas via the predictor system.

24 Claims, 13 Drawing Sheets

(51) Int. Cl.
*A61B 5/055* (2006.01)
*A61B 5/00* (2006.01)
*A61N 1/05* (2006.01)
*A61N 1/372* (2006.01)
*G01R 33/48* (2006.01)
*G06K 9/62* (2006.01)

(52) U.S. Cl.
CPC .......... *A61B 5/7264* (2013.01); *A61B 5/7275* (2013.01); *A61N 1/0534* (2013.01); *A61N 1/37252* (2013.01); *G01R 33/4806* (2013.01); *G06K 9/6224* (2013.01)

(58) Field of Classification Search
CPC .............. A61N 1/37252; G06K 9/6224; A61B 5/7264; A61B 5/0476; A61B 5/0484; A61B 5/4064; A61B 5/055; A61B 5/7203; A61B 5/7275; G01R 33/4806
See application file for complete search history.

(56) References Cited

U.S. PATENT DOCUMENTS

| | | | |
|---|---|---|---|
| 9,463,327 B2 | 10/2016 | Lempka et al. | |
| 10,603,498 B2 * | 3/2020 | Blum | A61N 1/36125 |
| 2011/0307030 A1 | 12/2011 | John | |
| 2012/0016435 A1 | 1/2012 | Rom | |
| 2012/0303089 A1 * | 11/2012 | Martens | A61N 1/36185 607/45 |
| 2013/0150922 A1 | 6/2013 | Butson et al. | |
| 2015/0119689 A1 | 4/2015 | Pascual-Leone et al. | |
| 2015/0360039 A1 | 12/2015 | Lempka et al. | |
| 2016/0001096 A1 | 1/2016 | Mishelevich | |
| 2016/0019693 A1 | 1/2016 | Silbersweig et al. | |
| 2016/0375248 A1 | 12/2016 | Carcieri et al. | |
| 2017/0304623 A1 | 10/2017 | Tandon | |
| 2018/0104500 A1 | 4/2018 | Blum et al. | |
| 2018/0199895 A1 | 7/2018 | Fiveland et al. | |
| 2018/0333582 A1 | 11/2018 | Grill et al. | |
| 2019/0142338 A1 | 5/2019 | Fang et al. | |

FOREIGN PATENT DOCUMENTS

| | | |
|---|---|---|
| WO | 2018023056 A1 | 2/2018 |
| WO | 2018157909 A1 | 9/2018 |
| WO | 2019094836 A1 | 5/2019 |

* cited by examiner

SYSTEMS AND METHODS FOR PREDICTING OPTIMAL DEEP BRAIN STIMULATION PARAMETERS

BACKGROUND OF THE INVENTION

Embodiments of the invention relate generally to a system and method for setting deep brain stimulation parameters, and more particularly to a system and method for predicting optimal deep brain stimulation parameters using brain network analytics.

Deep brain stimulation (DBS) is used for treating disabling neurological symptoms and psychiatric disorders. The procedure uses a neurostimulator to deliver electrical stimulation to the brain by way of surgically implanted electrodes. Depending on the condition being treated, the electrodes can be used to target certain cells within the brain or can be targeted toward areas of the brain that control movement or regulate abnormal impulses. For example, in this later case, the electrical stimulation can be used to disrupt abnormal nerve signals that cause tremor and/or other neurological symptoms. Over the past 20 years, more than 100,000 Parkinson's disease, essential tremor, dystonia and obsessive-compulsive disorder patients have seen significant symptom relief due to DBS treatment. Evidence now accumulates indicating that patients with chronic pain, post-traumatic stress disorder, and obesity may also benefit from DBS treatments.

Despite the long history of DBS, its underlying principles and mechanisms are still not clear. In particular, the understanding of how the brain responds to different DBS excitation parameters, such as electrode choice, frequency, current/voltage and pulse width is limited. While movement disorders such as Parkinson's disease provide immediate clinical feedback, most other disorders treated with DBS provide no real time feedback mechanism to let a clinician decide whether DBS has had its intended effect or whether the stimulation parameters are optimal for each individual patient. The immediate clinical feedback seen in Parkinson's disease patients is useful, but it is still unclear whether optimal settings (i.e., ceiling) has been achieved. Accordingly, the selection of optimal DBS excitation parameters that may best mitigate symptoms in a patient is largely based on trial and error. Specifically, existing methods for selection of optimal DBS excitation parameters are iterative processes that often requires numerous clinic visits by the patient to test the large number of possible stimulation parameters, with the patient being monitored over time to see how the patient evolves and determine if symptoms improve. This monitoring extends over a signification period of time, often 3-6 months or longer, resulting in a lengthy optimization period.

More recently, automated systems for parameter optimization have been proposed that use structural and functional MRI imaging to provide real time feedback to let a clinician decide whether DBS has had its intended effect or whether the stimulation parameters are optimal for each individual patient. That is, fMRI is used to provide a quick and efficient feedback mechanism by highlighting areas of brain activity related to DBS stimulation and allowing optimization of DBS stimulation parameters in close to real time. However, existing automated systems utilize an initial guess as to optimal set of parameter values that can result in feedback methods that converge to suboptimal local minima, thereby resulting in potential inaccuracies in the parameter optimization. Additionally, the existing automated systems can only perform the parameter optimization after DBS electrode implantation, using post-surgery structural and functional scans.

It would therefore be desirable to have a system and method that provides a more comprehensive solution for optimizing DBS excitation parameters. It would also be desirable for such optimization to not be limited to post-operative scans, but to be performed using imaging data pre-surgically, without DBS electrode implantation.

BRIEF DESCRIPTION OF THE INVENTION

In accordance with one aspect of the invention, a system for predicting optimal DBS parameters for a patient includes a DBS system controlled to send each of a plurality of DBS signals to one or more electrodes surgically implanted within one or more regions of a patient brain, wherein in sending the plurality of DBS signals the DBS system is controlled to perform a sweep of one or more DBS parameters, with each of the plurality of DBS signals comprising a different combination of DBS parameters. The system also includes a brain response acquisition system synchronized with the DBS system and controlled to collect brain response data resulting from each of the plurality of DBS signals. The system further includes a prediction system operably connected to the brain response acquisition system, the prediction system comprising a processor programmed to extract statistical metrics of brain response in the patient brain from the brain response data, access a DBS functional atlas comprising brain response maps derived from DBS treatment at optimal DBS parameter settings for a plurality of diseases, and predict optimal DBS parameters for the patient based on the statistical metrics of brain response and the DBS functional atlas.

In accordance with another aspect of the invention, a system for predicting optimal DBS parameters applied by one or more DBS electrodes for treatment of a patient includes a brain response acquisition system controlled to collect functional brain data from the patient in a resting state and a prediction system operably connected to the brain response acquisition system. The prediction system includes a processor programmed to estimate a functional connectome of the patient from the functional brain data, access a functional brain atlas comprising brain response maps for one or more disease-specific regions-of-interest (ROIs) or voxels, extract disease-specific graph theoretic metrics for one or more ROIs in the functional connectome using the functional brain atlas, and predict optimal DBS parameters for the patient using the disease-specific graph theoretic metrics.

In accordance with yet another aspect of the invention, a method for optimizing parameters of a DBS pulse signal applied by a DBS electrode for treatment of a patient includes inputting functional brain data into a predictor system, the functional brain data acquired responsive to a sweeping across one or more DBS parameters of a multi-dimensional parameter space of DBS parameters. The method also includes extracting statistical metrics of brain response from the functional brain data for one or more ROIs or voxels of the brain via the predictor system, accessing a DBS functional atlas comprising brain response maps derived from DBS treatment at optimal DBS parameter settings for a plurality of diseases via the predictor system, and predicting optimal DBS parameters for the patient based on the statistical metrics of brain response and the DBS functional atlas via the predictor system.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Figure 3:
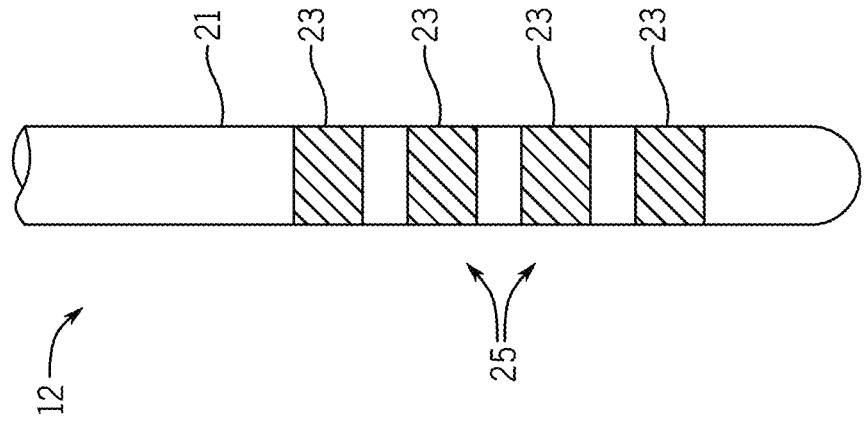
FIG. 3 is a schematic diagram of a DBS electrode useable with embodiments of the invention.

In general, embodiments of the invention described herein are directed to a system and method for optimizing deep brain stimulation parameters. According to one embodiment, brain response data is collected for each of a plurality of combinations of DBS parameters by sweeping through the multi-dimensional parameter space in synchronization with functional image acquisition of the brain response, with the brain response data from the patient being referenced against a brain response atlas to predict an optimal combination of DBS parameters for treatment of the patient. According to another embodiment, resting state brain response data is acquired for a patient via functional image acquisition, with a connectome being derived from the brain response data that is referenced against a brain response atlas to predict an optimal combination of DBS parameters for treatment of the patient.

As used herein, the terms "stimulation," "stimulated," "activation," and "activated" refer to any artificial input that causes one or more neuromodulatory effects (e.g., excitation/activation, inhibition, conduction block, modulation of response to other inputs, or the like) in at least a portion of neurons in a target tissue. The stimulation can be electrical stimulation and the target tissue can be neural tissue, such as a portion of the brain. Accordingly, the stimulation can be used for deep brain stimulation, according to an example embodiment.

As used herein, the terms "parameter," "parameter for stimulation," and "stimulus parameter" refer to a measure that can be one of a set of parameters that define the stimulation. In some instances, the parameters for stimulation can include voltage, frequency, and pulse width, as well as a stimulation configuration (e.g., which contact is selected to apply the stimulation and to what intensities, timing, etc.), with one or more of these parameters being selectively controlled.

As used herein, the term "imaging" can refer to a technique of creating a visual representation of the interior of a body for clinical analysis. Examples of medical imaging can include structural imaging and functional imaging. Structural imaging can reveal the underlying structure of at least a portion of the body. Functional imaging can provide direct or indirect measurements of physiological activity (e.g., neural activity). Examples of functional imaging modalities can include functional magnetic resonance imaging (fMRI), evoked potentials, local field potential (LFP), electrocorticography (ECoG), electroencephalography (EEG), magnetoencephalography (MEG), electromyography (EMG), positron emission tomography (PET), magnetic resonance spectroscopy (MRS), single-photon emission computed tomography (SPECT), near-infrared (NIR) spectroscopy, optical tomography (OT), ultrasound, laser Doppler measurements, and the like.

As used herein, the terms "optimal" and "sub-optimal" can be measures of clinical efficacy. For example, when a stimulation is deemed optimal, it can refer to a stimulation parameter being used that produces a stimulation with a clinically relevant outcome. When a stimulation is deemed sub-optimal, it can refer to a stimulation parameter being used that produces a stimulation with an outcome below clinical relevance. For example, in some instances, a sub-optimal stimulation is 10% or more different than a clinically relevant stimulation. In some instances, a sub-optimal stimulation is 5% or more different than a clinically relevant stimulation.

As used herein, the term "disease" is meant to refer to any neurological condition, neurological symptom, or psychiatric disorder that is suitable for treatment by functional neurosurgery, such as DBS.

Figure 1:
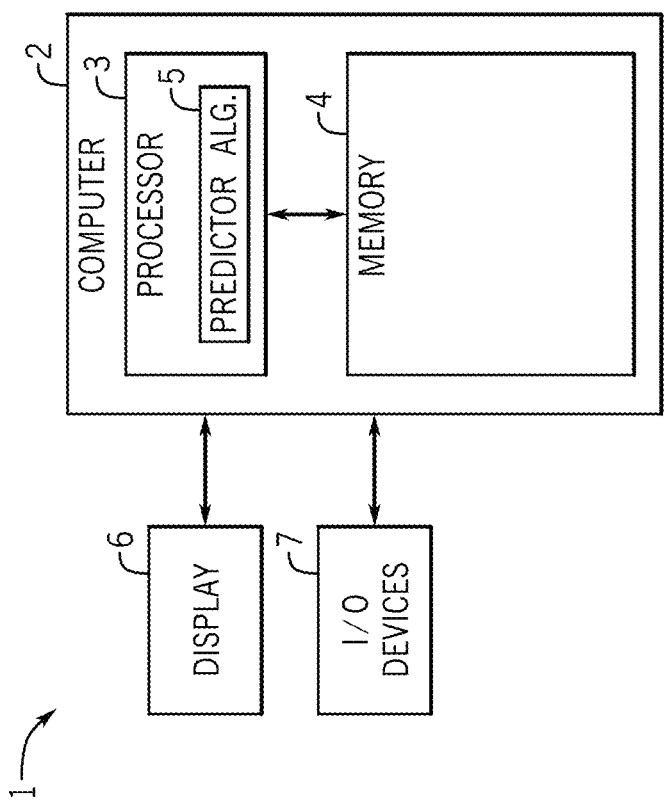
FIG. 1 is a schematic block diagram of a system for predicting optimal DBS parameters for DBS patient treatment, according to an embodiment of the invention.

Referring to FIG. 1, an example of a basic system 1 for predicting optimal DBS parameters for a patient of interest is illustrated, in accordance with an embodiment of the invention. The system 1 is depicted as being implemented using a computer 2 that is programmed and/or configured to predict optimal DBS parameters according to an aspect of the invention. The computer 2 can be a workstation, a standalone computer, a notebook computer, or it can be implemented as part of other microprocessor-based equipment that is programmed based on the teachings contained herein.

The computer 2 includes a processor 3 that is operative to execute instructions for performing the methods described herein. The instructions can be stored in associated memory 4. In the example of FIG. 1, the processor 3 is depicted as running a predictor algorithm 5. Such predictor algorithm 5 can be stored in the memory 4 and loaded into the processor 3 for predicting optimal DBS parameters for patient treatment. As used herein, the optimal DBS parameters represent one or more of a voltage, frequency, pulse width, and DBS electrode contact used for applying a DBS signal/treatment, that can be selectively controlled to achieve an optimal therapeutic effect.

The system 1 can also include a display 6 that can be utilized to represent the results and calculations performed by the predictor algorithm, as well as one or more other input or output devices 7. Such devices 7 can provide an interface through which a user can input data as well as control the predictor algorithm 5. For example, a user can employ the I/O device 7 to input data, such as instructions to initiate or modify the predictor algorithm procedure. A user can also employ the I/O device 7 to set the range of parameters, the granularity of such parameters as well as to program other parameters being used in the procedure. The I/O device 7 can also be utilized to interface and enable acquisition of data (e.g., imaging data) from an associated imaging device, such as a magnetic resonance imaging (MRI) system, a computer tomography (CT) system or other imaging or acquisition modality that can provide data on a functional brain response responsive to DBS. Still further, the I/O device can be employed to access a brain atlas database, such as from another location in the memory 4 or from another storage location or device.

Figure 2:
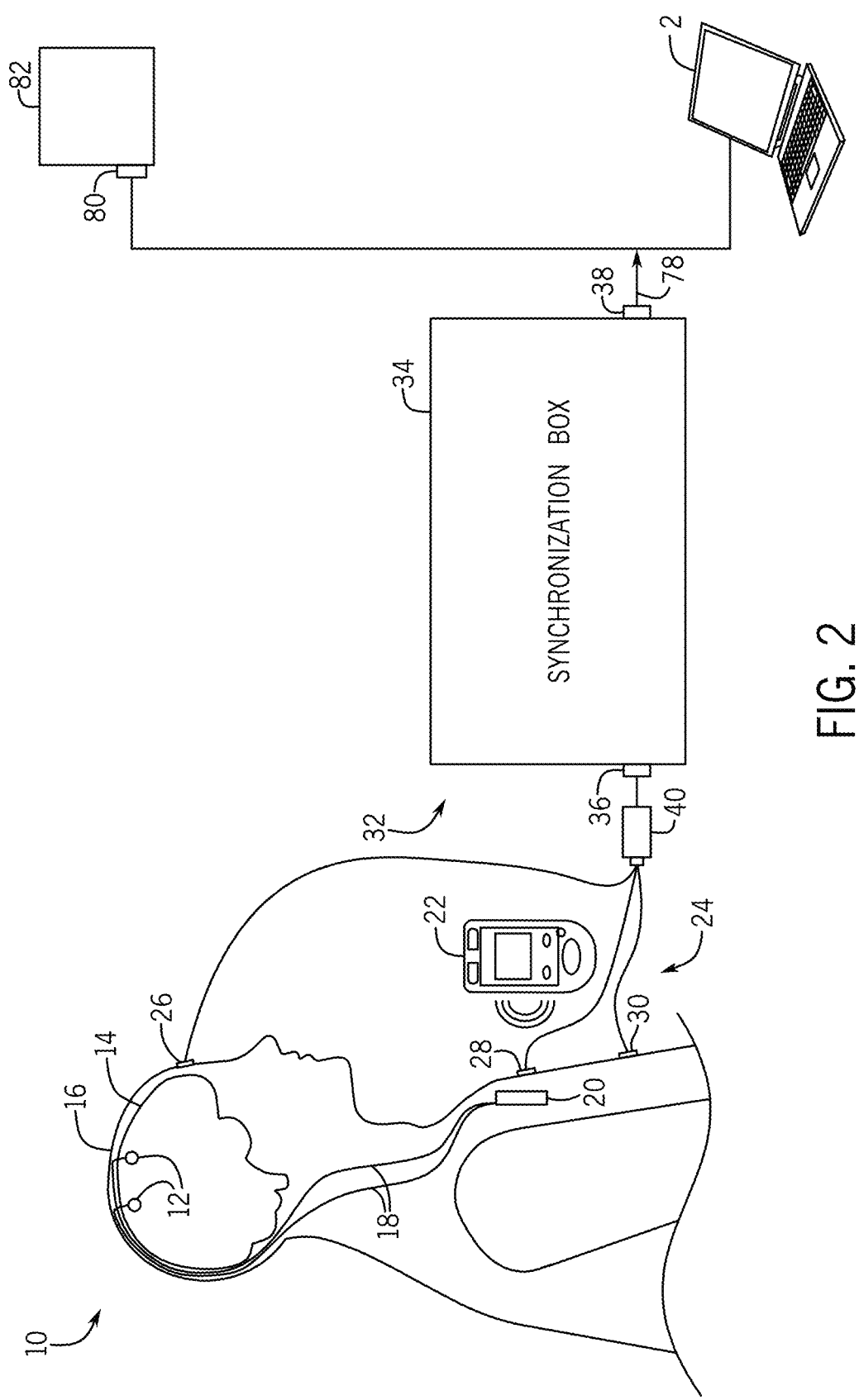
FIG. 2 is a schematic diagram of a deep brain stimulation (DBS) treatment and detection system usable with the system of FIG. 1, according to an embodiment of the invention.

Referring now to FIG. 2, a deep brain stimulation (DBS) treatment and detection system 10 is illustrated that is usable with embodiments of the invention. The DBS system 10 includes one or more leads or electrodes 12 surgically implanted within one or more regions of the brain 14 of a patient 16. Each implanted electrode 12 is configured to apply stimulation signals to a targeted region of the brain 14. While two electrodes 12 are illustrated in FIG. 1, it will be understood that system 10 may include a single implanted electrode as well as three or more electrodes, each of which may be positioned and configured to facilitate unipolar or bipolar stimulation.

Each implanted electrode 12 is connected through an extension wire 18 that is passed under the skin of the patient 16 to a pulse generator 20 configured to deliver stimulation signals to electrodes 12. Pulse generator 20 may include a power supply (not shown) such as a battery or other type of power storage device and microelectronic circuitry (not shown) that may include hardware and/or software for generating and outputting stimulation signals in response to control signals or commands. In some embodiments, pulse generator 20 may further include a storage unit (not shown) that permits patient-specific data to be stored within the pulse generator 20.

In the illustrated embodiment, pulse generator 20 is an internal pulse generator that is implanted beneath the skin of the patient 16, such as, for example, under the clavicle as shown in FIG. 1. However, internal pulse generator 20 may be located elsewhere within the patient 16 in alternative embodiments such as, for example, lower in the chest or over the abdomen. In alternative embodiments, pulse generator 20 may be an external device coupled to implanted electrodes 12.

In the case of an implanted pulse generator, the pulse generator 20 is programmed with a wireless device 22 that is held over the skin of the patient 16 proximate the implanted location of the pulse generator 20. The programming defines the excitation parameters of the DBS, which can be adjusted as the patient's condition changes over time. The circuitry within the pulse generator 20 generates pulse sequences in accordance with the stimulation parameters that send excitation signals to implanted electrodes 12. The stimulation can be provided in a continuous or cycling fashion and at various voltages, frequencies, and pulse widths, based on the desired treatment. Additionally, different contacts of the electrodes 12 may be activated to apply the stimulation, as illustrated in FIG. 3, where an electrode 12 is shown in greater detail as including a housing 21 extending along a length thereof and a plurality of contacts 23 positioned along a length of electrode 12 and housing 21 at a plurality of defined contact levels 25. Each contact level 32 may have two or more contacts 23 located at different angular positions around the circumference of housing 21. According to embodiments of the invention, and as will be explained in greater detail in the application, the pulse generator 20 may be programmed (either directly or via wireless device 22) to generate pulse sequences that sweep through the multi-dimensional DBS parameter space, including sweeping through one or more of voltages, frequencies, pulse widths, and different contacts of the electrodes 12.

Referring again to FIG. 2, a sensor system 24 is provided to sense and track the stimulation signal transmitted by the internal pulse generator 20 to the implanted electrodes 12. In one embodiment, sensor system 24 is an arrangement of three EKG electrodes 26, 28, 30 that are affixed to the skin surface of the patient 16 to measure bioelectrical signals from the patient 16, which include physiological signals generated by the patient's anatomy (e.g., the heart) and voltages generated by the small currents flowing through the patient 16 as a consequence of the DBS. In the illustrated embodiment, EKG electrodes 26, 28, 30 are applied to the patient 16 proximate the forehead, near the internal pulse generator 20, and abdomen respectively and may be used to sense a DBS excitation pattern generated by implanted electrodes 12 configured for bipolar and/or monopolar operation modes. However, a skilled artisan will recognize that EKG electrodes 26, 28, 30 may be positioned in alternative locations on the patient 16 such as on the multiple locations on the chest or left arm, right arm, and at a reference location, as non-limiting examples, in embodiments that utilize electrodes 12 configured for monopolar operation. In yet alternative embodiments, sensor system 24 may include sensors provided in the form of loops or plates (not shown) that are configured to pick up the DBS signals through inductive or capacitive coupling to the internal pulse generator 20.

A synchronization box 32 is used in conjunction with the sensor system 24 to detect the DBS excitation pattern generated by the internal pulse generator 20 and transform the detected signal into a pulse sequence that emulates the detected pattern. Synchronization box 32 includes a housing 34 with at least one input port 36 and at least one output port 38. A bio-amplifier 40 is coupled between sensor system 24 and the input port 36 of synchronization box 32 to electrically isolate the patient 16 from the synchronization box 32 and amplify the incoming signal from EKG electrodes 26, 28, 30. In an alternative, embodiment bio-amplifier 40 may be integrated within the housing 34 of synchronization box 32.

The synchronization box 32 is configured to transform bioelectrical signals received from sensor system 24 into a series of pulses that represent predicted active periods and non-active periods of a cyclic deep brain stimulation. In one embodiment, the output of synchronization box 32 is in the form of a log of time stamps that predict the start time and duration of future active transmission periods of neurological excitation. In another embodiment, the output generated by synchronization box 32 is in the form of a series of timing pulses. The timing pulses of the output signal simulate the envelope of the cyclic DBS excitation pattern, with the pulse width of each timing pulse approximating the duration of an active or ON portion of a respective ON/OFF cycle.

Data measured in real time, including the time stamps of the measured and predicted pulses can be output from the synchronization box 32 via output port 38 of synchronization box 32—such that data corresponding to the detected DBS excitation pattern received from sensor system 24 and a digital logic pulse or output timing signal 78 generated by synchronization box 32 are provided via output port 38. According to one embodiment, the output port 38 of synchronization box 32 is coupled to an auxiliary trigger input or input data acquisition board 80 of an imaging device 82, such as the auxiliary input 84 of MRI scanner 86 illustrated in FIG. 3, and is used to trigger the start of an image data acquisition sequence such as, for example, an fMRI scan, in order to provide for alignment of DBS electrode stimulation periods with fMRI scan data acquisition. According to one embodiment, the output port 38 of synchronization box 32 is coupled to computer 2 (FIG. 1) such that data corresponding to the detected DBS excitation pattern received from sensor system 24 and a digital logic pulse or output timing signal 78 generated by synchronization box 32 are provided thereto. While synchronization box 32 is depicted as a standalone device in FIG. 1, it is contemplated that the components or the software equivalents thereof can be incorporated directly within imaging device 82 in an alternative embodiment.

While the above DBS system 10 is described as including synchronization box 32 in order to provide for alignment of DBS electrode stimulation periods with fMRI scan data acquisition when using an ON/OFF DBS cycling, it is recognized that synchronization box 32 would not be required if continuous DBS is applied. That is, Mill scan data could be acquired with the DBS constantly firing at two different settings and comparing their connectivity; in which case synchronization box 32 is not required, as the continuous DBS and Mill scan data acquisition would inherently be synchronous with one another.

Figure 4:
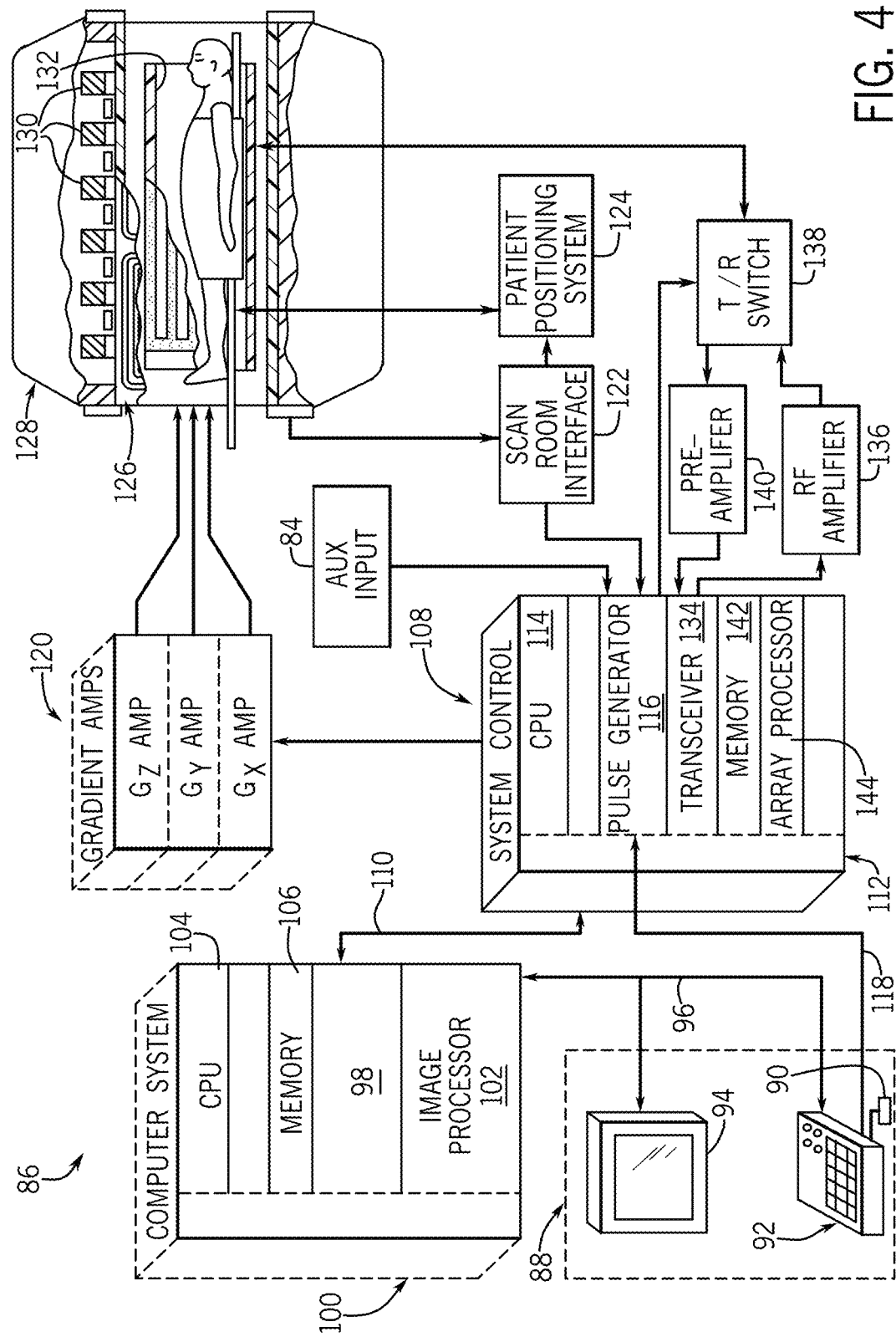
FIG. 4 is a schematic diagram of an exemplary MR imaging system usable with the system of FIG. 1, according to an embodiment of the invention

Referring now to FIG. 4, the major components of an MRI scanner 86 useable with the DBS system 10 of FIG. 2 are shown according to an exemplary embodiment of the invention. The operation of the MRI scanner 86 is controlled for certain functions from an operator console 88, which in this example includes a keyboard or other input device 90, a control panel 92, and a display screen 94. The operator console 88 communicates through a link 96 with a separate computer system 98 that enables an operator to control the production and display of images on the display screen 94. The computer system 98 includes a number of modules which communicate with each other through a backplane 100. These modules include an image processor module 102, a CPU module 104 and a memory module 106, known in the art as a frame buffer for storing image data arrays. The computer system 98 communicates with a separate system control 108 through a high-speed serial link 110. The input device 90 can include a mouse, joystick, keyboard, track ball, touch activated screen, light wand, voice control, card reader, push-button, or any similar or equivalent input device, and may be used for interactive geometry prescription.

The system control 108 includes a set of modules connected together by a backplane 112. These include a CPU module 114 and a pulse generator module 116 which connects to the operator console 88 through a serial link 118. It is through serial link 118 that the system control 108 receives commands from the operator to indicate the scan sequence that is to be performed. The pulse generator module 116 operates the system components to carry out the desired scan sequence and produces data which indicates the timing, strength and shape of the RF pulses produced, and the timing and length of the data acquisition window. The pulse generator module 116 connects to a set of gradient amplifiers 120, to indicate the timing and shape of the gradient pulses that are produced during the scan. The pulse generator module 116 can also receive timing data through an auxiliary trigger input 84, which may be coupled to output of the synchronization box 32 of FIG. 1. And finally, the pulse generator module 116 connects to a scan room interface circuit 122 which receives signals from various sensors associated with the condition of the patient and the magnet system. It is also through the scan room interface circuit 122 that a patient positioning system 124 receives commands to move the patient to the desired position for the scan.

The gradient waveforms produced by the pulse generator module 116 are applied to the gradient amplifier system 120 having Gx, Gy, and Gz amplifiers. Each gradient amplifier excites a corresponding physical gradient coil in a gradient coil assembly generally designated 126 to produce the magnetic field gradients used for spatially encoding acquired signals. The gradient coil assembly 126 forms part of a resonance assembly 128 which includes a polarizing magnet 130 and a whole-body RF coil 132. A transceiver module 134 in the system control 108 produces pulses which are amplified by an RF amplifier 136 and coupled to the whole-body RF coil 132 by a transmit/receive switch 138. The resulting signals emitted by the excited nuclei in the patient may be sensed by the same whole-body RF coil 132 and coupled through the transmit/receive switch 138 to a preamplifier 140. The amplified MR signals are demodulated, filtered, and digitized in the receiver section of the transceiver module 134. The transmit/receive switch 138 is controlled by a signal from the pulse generator module 116 to electrically connect the RF amplifier 136 to the whole-body RF coil 132 during the transmit mode and to connect the preamplifier 140 to the whole-body RF coil 132 during the receive mode. The transmit/receive switch 138 can also enable a separate RF coil (for example, a surface coil) to be used in either the transmit or receive mode.

The MR signals picked up by the whole-body RF coil 132 are digitized by the transceiver module 134 and transferred to a memory module 142 in the system control 108. A scan is complete when an array of raw k-space data has been acquired in the memory module 142. This raw k-space data is rearranged into separate k-space data arrays for each image to be reconstructed, and each of these is input to an array processor 144 which operates to Fourier transform the data into an array of image data. This image data is conveyed through the serial link 110 to the computer system 98 where it is stored in memory. In response to commands received from the operator console 88 or as otherwise directed by the system software, this image data may be archived in long term storage or it may be further processed by the image processor module 102 and conveyed to the operator console 88 and presented on the display screen 94.

Operation of MRI scanner 86 to acquire fMRI scan data study produces a chronologically ordered sequence (or "time series") of MM (magnetic resonance imaging) images, each of which represents a three-dimensional "snapshot" of the subject's brain volume at a unique time at which the image was recorded. Each 3D representation of the subject's brain volume shows a level of neuronal activation at the image's recording time at each three-dimensional point comprised by the brain volume. A difference between two activation levels may be represented in the image as a corresponding difference in color, brightness, density, or another characteristic of a voxel of the image. In some implementations, a level of activation of a region of a brain volume may be a function of a blood oxygenation level dependent (BOLD) signal that identifies a level of neuronal activation in that region. An fMRI series may be further analyzed to identify couplings between regions of a brain that may work together to perform a particular type of function or to respond to a specific class of stimulus, a relationship known as "functional connectivity." Such relationships may in some cases be inferred from correlations or covariances among time measurements associated with changes in levels of activation of such regions. If two regions, for example, activate simultaneously every time a subject receives a DBS signal, those two regions may be deemed to be functionally connected.

According to an embodiment of the invention, the DBS system 10 of FIG. 2 and the MRI scanner 86 of FIG. 4 may be employed in order to predict an optimal combination of DBS parameters that can be applied to obtain ideal symptom relief for a patient. The DBS system 10, and more specifically pulse generator 20 and electrodes 12, are controlled to stimulate the patient using a plurality of different combinations of DBS parameters, with this plurality of different combinations of DBS parameters providing a sweeping through of all possible combinations of DBS parameters that might be employed. For example, DBS system 10 can utilize regular patterns of continuous or cycling stimulation with rectangular biphasic waveforms, with one or more of voltage, pulse width, frequency, and the electrode contacts used to apply the stimulation waveform being modified. For each of these combinations of DBS parameters, brain response data is collected through fMRI data acquisition, with the fMRI data acquisition being synchronized (in the case of cycling stimulation) with the stimulation provided by the DBS electrodes.

Figure 5:
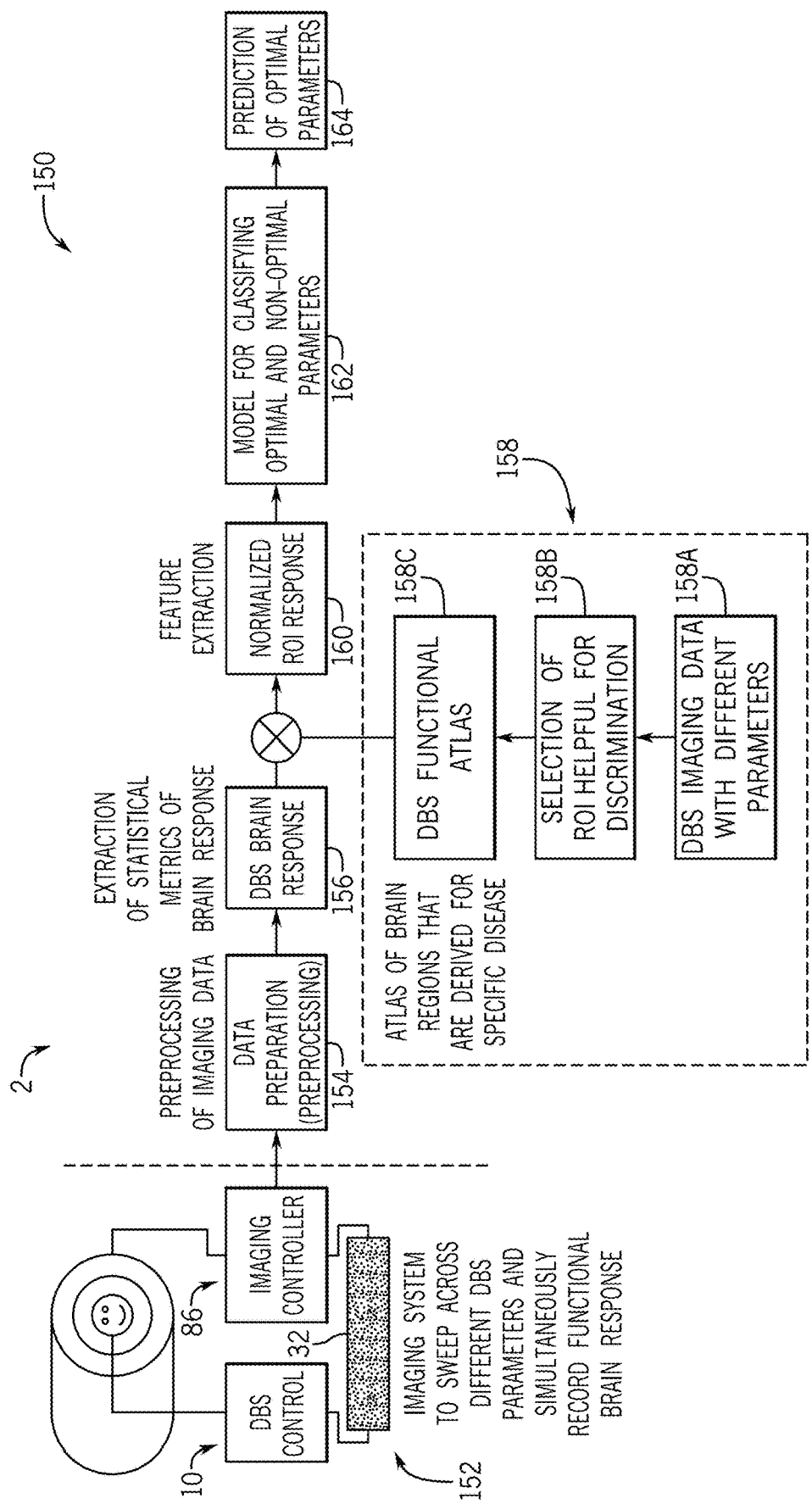
FIG. 5 is a flowchart illustrating a technique for predicting optimal DBS parameters for DBS patient treatment, according to an embodiment of the invention.

Referring now to FIG. 5, a functional block diagram is provided that illustrates a method 150 for predicting an optimal combination of DBS parameters that can be applied to obtain ideal symptom relief for a patient. The method 150 may be implemented by a system 2 such as illustrated in FIG. 1, for example, when provided inputs thereto from DBS system 10 and/or MM apparatus 86, with one or more processors 3 of computer 2 in such a system performing steps and functions described hereafter to predict such an optimal combination of DBS parameters to be applied by electrodes 12. Alternatively, it is recognized that the method 150 may be implemented by computer system 98 on MM scanner 86, according to another embodiment.

As illustrated in FIG. 5, DBS system 10 and MRI scanner 86 are provided to apply DBS stimulation and acquire brain response data, with the systems being simultaneously controlled via synchronization box 32 that links the systems together and provides for synchronization therebetween. Brain response data, in the form of fMRI data acquired by MM scanner 86, is gathered at STEP 152 for each of a plurality of different combinations of DBS parameters applied when performing a sweep through of all possible combinations of DBS parameters that might be employed during stimulation. According to an exemplary embodiment, the combinations of DBS parameters used for the stimulations is randomized, so as to reduce any effect the history of stimulations might have, such as if an ordered set of DBS parameter combinations is used. Cycling On and Off of the DBS stimulation may be performed between each combination of DBS parameters, such as via implementation of a 30 second On/Off cycling paradigm, depending on the experimental method choices.

At STEP 154, preprocessing of the brain response data acquired at STEP 152 is performed to remove artifacts and prepare the functional image data for subsequent analysis and processing steps. In numerous embodiments, preprocessing can be used to standardize image data to known reference images. For example, in several embodiments, fMRI image data can be preprocessed to yield time-series sequence of image data in which brain structures and/or regions within the preprocessed time-series can be identified by the image processing system. According to one embodiment, preprocessing includes realigning and unwarping image data, and despiking image data with respect to movement, variance, and/or any source of noise artifacts as appropriate to the requirements of a given application. In many embodiments, spikes with respect to variance are the result of extreme responses, such as, but not limited to, periods of very high activity followed by periods of very low activity. Preprocessing may further include applying linear co-registration to identified structures in the image data. Realigning and unwarping image data can be used to remove movement artifacts from a fMRI scan time-series of images. Methods for realigning and unwarping image data that can be used in accordance with several embodiments of the invention can be found in the Statistical Parametric Mapping (SPM) library by the Wellcome Trust Centre for Neuroimaging of University College London, London, England or other versions of SPM, such as SPM12. Still further, linear co-registration can be performed using FSL software library of by the Oxford Centre for Functional MRI of the Brain of the University of Oxford (FMRIB), Oxford, England. While a specific method for preprocessing image data is described above, any number of steps could be incorporated for preprocessing image data in accordance with the requirements of a given application.

Upon completion of the brain response data preprocessing, the method 150 continues to STEP 156 where statistical brain response maps (i.e., statistical metrics of brain response) comparing, for example, DBS On/Off or two different settings are estimated from the preprocessed data, such as using a 30 second DBS On/Off block design. The statistical brain response maps indicate which regions and/or structures of the brain become active or are non-active in response to DBS stimulation. In one embodiment, statistical metrics are determined region-by-region in the brain to identify particular regions of interest (ROI), such as individual structures and/or groups of structures, and an average activation (i.e., mean t-values for activation and deactivation) in one or more of these ROIs may be extracted. The statistical brain response maps may be generated from extracted brain data, with regression and smoothing techniques being applied to aid in extraction of such data.

In conjunction with the statistical brain response maps extracted at STEP 156, method 150 also references a DBS functional atlas comprised of brain response maps at optimal DBS parameter settings for various diseases, as indicated at STEP 158. As used herein, "disease" is meant to refer to any neurological condition, neurological symptom, or psychiatric disorder that is suitable for treatment by functional neurosurgery, such as DBS. The atlas can be constructing using a variety of techniques, including weighted sum, discriminant analysis, etc. In constructing the DBS functional atlas, functional imaging data is acquired/collected from a large cohort of patients (e.g., hundreds or thousands of patients) at different (optimal and non-optimal) DBS parameter combinations (158A), from which one or more ROIs may be selected (158B) that are useful for discrimination (i.e., a linear discriminant analysis (LDA)). Individual voxels may also be used for discrimination. A disease-specific DBS functional atlas may thus be derived (158C) that reflects brain activation patterns for optimal and non-optimal DBS parameters, with brain activation patterns/brain response maps being identified that correlate with an optimal therapeutic effect in the patient, i.e., that achieve maximal behavioral symptom relief and avoid unwanted side-effects, thereby serving as an objective proxy for DBS efficacy.

Based on the statistical brain response maps and the DBS functional atlas acquired/referenced at STEPS 156, 158, features may be extracted from the brain response maps at STEP 160. For example, normalized mean t-values for activation and deactivation may be calculated from the statistical response maps and DBS functional atlas for ROIs (motor and non-motor), so as to obtain a normalized ROI response. Other features such as connectivity strength, for example z-scores, may also be used. The extracted features may then be fed into a predictive machine learning model (derived/built from the DBS functional atlas), as indicated at STEP 162, that is able to classify optimal and non-optimal DBS parameters, and/or rank DBS parameters at an individual patient level using for example a linear discriminant analysis (LDA). The machine learning model functions to output a prediction of optimal DBS parameter, as indicated at STEP 164. Optionally, these optimal DBS parameters may then be provided/input to DBS system 10 (i.e., to pulse generator 20 and/or wireless device 22) to cause the electrode(s) 12 to apply DBS signals to the patient having the optimal DBS parameters, so as to achieve a best symptom relief for the patient.

Accordingly, the method 150 may be performed to predict the optimal combination of DBS parameters for best symptom relief and least adverse effects for an individual patient. The patient's fMRI responses are fed into the machine learning model created with the retrospective DBS functional atlas data to provide an accurate prediction of the optimal DBS parameters. With the automated method 150, the time for DBS parameter optimization may be reduced from 3-6 months to a single session.

Figure 6:
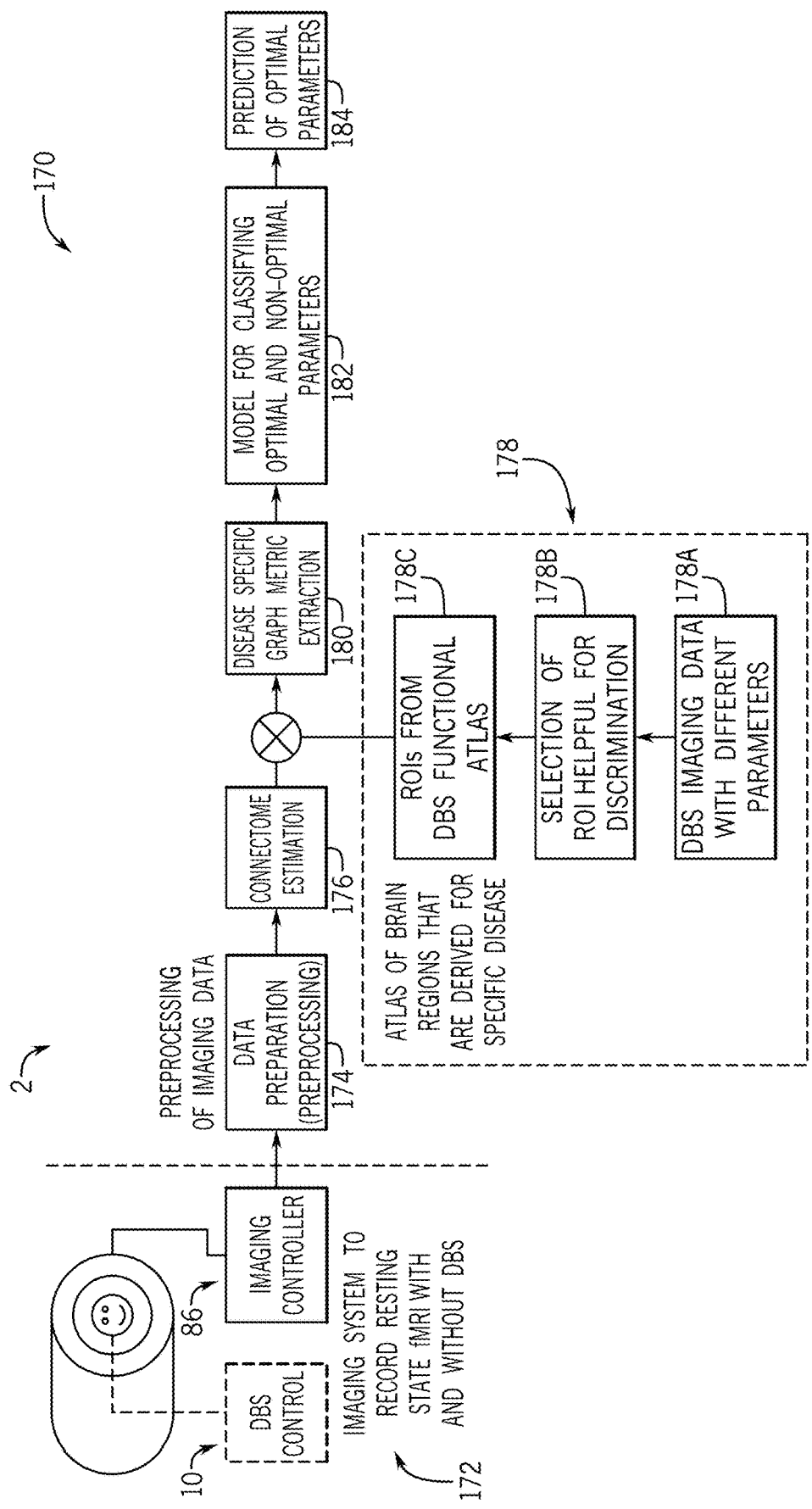
FIG. 6 is a flowchart illustrating a technique for predicting optimal DBS parameters for DBS patient treatment, according to another embodiment of the invention.

While embodiments of the invention described so far make reference to post-surgery electrode implantation in the patient that enables a sweeping of DBS parameters to be performed as part of predicting an optimal combination of DBS parameters that can be applied to obtain ideal symptom relief, embodiments of the invention also extend to methods for predicting such an optimal combination of DBS parameters prior to a DBS implantation surgery. Referring now to FIG. 6, a functional block diagram is provided that illustrates a method 170 for predicting an optimal combination of DBS parameters that can be applied to obtain ideal symptom relief for a patient, with such predictions being provided without DBS data for the patient (that is, the method is performed prior to DBS implantation). The method 170 may be implemented by a system 2 such as illustrated in FIG. 1, for example, when provided inputs thereto from MRI apparatus 86, with one or more processors 3 of computer 2 in such a system performing steps and functions described hereafter to predict such an optimal combination of DBS parameters to be applied by electrodes 12. Alternatively, it is recognized that the method 170 may be implemented by computer system 98 on MRI scanner 86, according to another embodiment.

As illustrated in FIG. 6, MRI scanner 86 is provided to acquire resting state fMRI data (rs-fMRI) of a patient at STEP 172, with such rs-fMRI data being acquired in a known fashion. At STEP 174, preprocessing of the rs-fMRI data is performed to remove artifacts and prepare the rs-fMRI data for subsequent analysis and processing steps. In numerous embodiments, preprocessing can be used to standardize image data to known reference images. For example, in several embodiments, rs-fMRI data image data can be preprocessed to yield time-series sequence of image data in which brain structures and/or regions within the preprocessed time-series can be identified by the image processing system. According to one embodiment, preprocessing includes realigning and unwarping image data, and despiking image data with respect to movement, variance, and/or any source of noise artifacts as appropriate to the requirements of a given application. In many embodiments, spikes with respect to variance are the result of extreme responses, such as, but not limited to, periods of very high activity followed by periods of very low activity. Preprocessing may further include applying linear co-registration to identified structures in the image data. Realigning and unwarping image data can be used to remove movement artifacts from a fMRI scan time-series of images.

Upon completion of the rs-fMRI data preprocessing, the method continues to STEP 176 where a brain network connectome (i.e., brain connectivity model) estimation is performed. In one embodiment, and prior to connectome estimation, the preprocessed image data can be passed through additional connectivity preprocessing steps to enable accurate measurements of time-series data. As examples of such connectivity preprocessing, slice time correction can be performed and image data can be normalized to a coordinate system (e.g., Montreal Neurological Institute (MNI) coordinate system or Talairach coordinate system) in order to define regions of the brain, with a spatial smoothing then being performed. According to embodiments, the connectome can include psychophysical interaction (PPI) models, ROI resting state models, and voxel wise resting state models. PPI models can describe connectivity between a ROI (or voxel) and other brain regions, thereby indicating the brain regions where the activity depends on the psychological context and the physiological state of the ROI (or voxel). Resting state models are used to estimate the resting state of a particular ROI, or a region defined by a voxel or set of voxels. The connectome generated at STEP 176 thus provides a comprehensive map of neural connections in the brain that may be used to indicate responsiveness to applied stimuli.

In conjunction with the connectome output at STEP 176, method 170 also references a functional atlas comprised of brain functioning/responses prior to a DBS implantation surgery (i.e., resting state) and brain responses for all combinations of DBS parameter settings post-DBS implantation surgery, as indicated at STEP 178. The atlas can be constructing using a variety of known techniques, including weighted sum, discriminant analysis, etc. In constructing the functional brain atlas, functional imaging data is acquired/collected from a large cohort of patients (e.g., hundreds or thousands of patients) at different (optimal and non-optimal) DBS parameter combinations and without DBS implantation (178A), from which one or more ROIs (or voxel) may be selected (178B) that are useful for discrimination (e.g., a linear discriminant analysis (LDA)). A disease-specific functional atlas may thus be derived (178C) from which disease-specific ROIs (or voxel) may be identified. The disease-specific ROIs (or voxel) identified for this large cohort of patients may thus provide a correlation between non-DBS, resting state brain activation patterns and brain activation patterns for optimal and non-optimal DBS parameters post-DBS electrode implantation.

Based on the connectome and the functional brain atlas acquired/referenced at STEPS 176, 178, disease-specific graph metric extraction may be performed at STEP 180. That is, graph theoretic brain network metrics for the ROIs (or voxel) will be calculated for the functional connectome. Using graph theoretic metrics, ROIs (or voxel) can be represented by vertices in a graph, and some measure of connectivity between those ROIs (or voxel) can be represented by edges, with simple, numerical summary descriptors of graph organization being derived that describe the graph structure or topology in terms of the brain network (e.g., characteristic path length, clustering coefficient, and small-worldness, for example)—with these metrics providing a way to characterize the underlying functional and structural brain networks and allow comparisons across time, subjects, or groups of subjects. The extracted disease-specific graph metrics are then input to a predictive machine learning model, as indicated at STEP 182, that is able to classify optimal and non-optimal DBS parameters and/or rank DBS parameters at an individual patient level, with the machine learning model functioning to output a prediction of optimal DBS parameter at STEP 184.

Accordingly, the method may be performed to determine if the patient is a suitable candidate for DBS treatment and, if so, to enable identification of DBS parameters that provide an optimal therapeutic effect in the patient, i.e., that achieve maximal behavioral symptom relief and avoid unwanted side-effects. The patient's fMRI responses are fed into the machine learning model created with the retrospective functional brain atlas data to provide an assessment of patient suitability for DBS treatment and an accurate prediction of the optimal DBS parameters.

Figure 7:
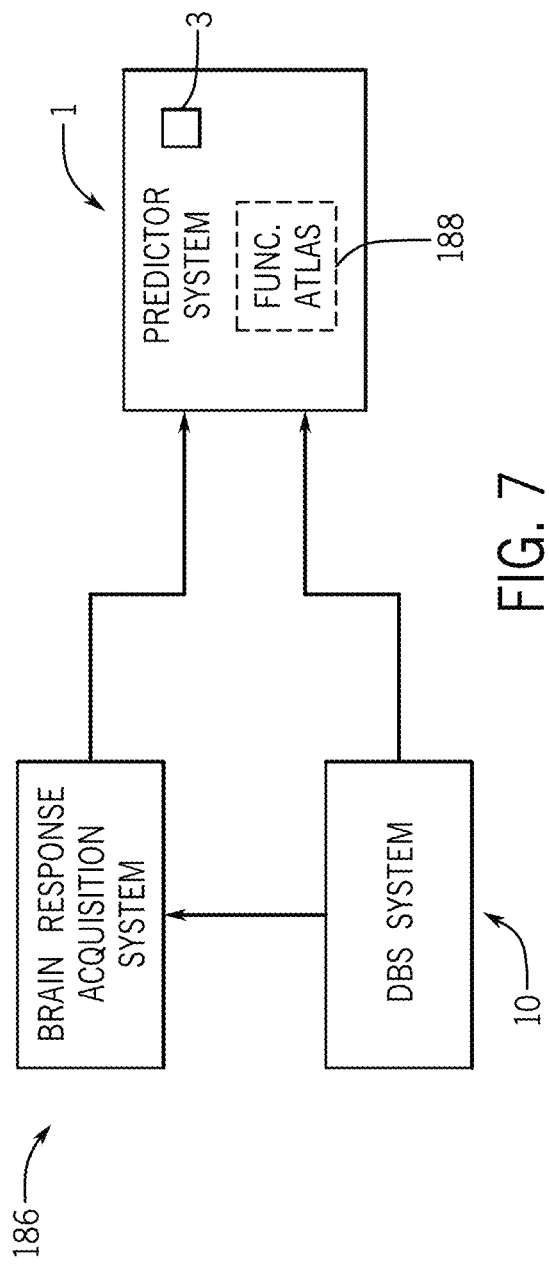
FIG. 7 is a schematic block diagram of a predictor system, DBS system, and brain response acquisition system forming a collective system for predicting optimal DBS parameters for DBS patient treatment, according to an embodiment of the invention.

Referring now to FIG. 7, a block schematic diagram of a system 186 for predicting optimal DBS parameters for a patient is illustrated. Included in the system 186 is a predictor system 1 such as shown in FIG. 1, a DBS system 10 such as shown in FIG. 2, and a brain response acquisition system 86 that, according to an exemplary embodiment, is an MRI scanner 86 as shown in FIG. 4. The predictor system 1, DBS system 10, and brain response acquisition system 86 are operatively connected to one another to provide for predicting optimal DBS parameters for a patient.

According to one embodiment, and as explained in detail above with respect to FIG. 5, the DBS system 10 is controlled to send each of a plurality of DBS signals to one or more electrodes 12 (FIG. 2) surgically implanted within one or more regions of a patient brain, wherein in sending the plurality of DBS signals, the DBS system 10 is controlled to perform a sweep of one or more DBS parameters, with each of the plurality of DBS signals comprising a different combination of DBS parameters. The brain response acquisition system 86 is synchronized with the DBS system 10 and controlled to collect brain response data resulting from each of the plurality of DBS signals. The prediction system 1 comprises a processor 3 programmed to extract statistical metrics of brain response in the patient brain from the brain response data, access a DBS functional atlas 188 (stored in predictor system 1, as shown in FIG. 7, or in a database accessible thereby) comprising brain response maps derived from DBS treatment at optimal DBS parameter settings for a plurality of diseases or neurological conditions, and predict optimal DBS parameters for the patient based on the statistical metrics of brain response and the DBS functional atlas. The DBS parameters swept by the DBS system 10 and the optimal DBS parameters predicted by the prediction system 1 comprise one or more of signal voltage, frequency, pulse width, and an activated contact selected from a plurality of contacts 23 on each of the one or more electrodes 12 (FIG. 3).

According to another embodiment, and as explained in detail above with respect to FIG. 6, the brain response acquisition system 86 is controlled to collect functional brain data from a patient in a resting state. The prediction system 1, i.e., processor 3 thereof, is programmed to estimate a functional connectome of the patient from the functional brain data (as derived from data acquired by brain response acquisition system 86), access a functional brain atlas 188 comprising brain response maps for one or more disease-specific regions-of-interest (ROIs) or voxels, extract disease-specific graph theoretic metrics for one or more ROIs in the functional connectome using the functional brain atlas 186, and predict optimal DBS parameters for the patient using the disease-specific graph theoretic metrics. The predicted optimal DBS parameters comprise one or more of signal voltage, frequency, pulse width, and an activated contact selected from a plurality of contacts 23 on each of the one or more electrodes 12 (FIG. 3).

Example 1

The example described below refers to treatment of patients suffering from Parkinson's disease (PD) in the subthalamic nucleus (STN) and deemed a candidate for DBS therapy. As stated above, embodiments of the invention are directed to a system and method for predicting a set or combination of DBS parameters that provide an optimal therapeutic effect in the patient—i.e., optimal DBS parameters. In the example illustrated here below, the electrode contacts ON for the DBS were cycled, while the voltage, frequency, and pulse-width remained constant; however, as described above, it is recognized that exemplary embodiments of the invention are directed to methods where a sweep of one or more of the voltage, frequency, pulse-width, and contact used are performed—i.e., a sweep across a multi-dimensional parameter space of DBS parameters.

Figure 8:
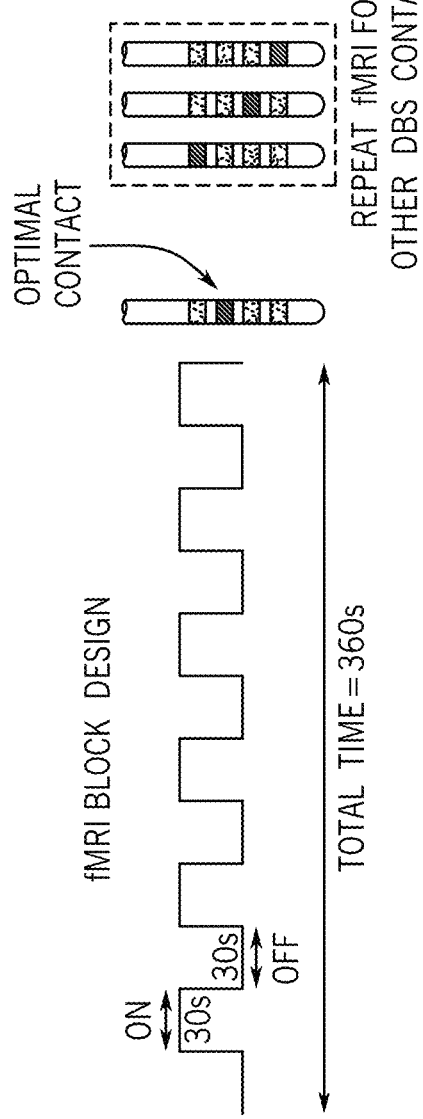
FIG. 8 illustrates fMRI sequences acquired using a 30 s DBS-OFF/ON cycling paradigm, along with optimal and non-optimal DBS electrode activation.

In performing a method to output this prediction, the method was conducted in two phases. In the retrospective phase, fMRI was acquired in twenty-four patients with a priori clinically optimized DBS programming. In the prospective phase, fMRI was acquired in four patients prior to establishing optimal DBS settings. fMRI sequences were acquired in six-minute blocks on a 3T MM scanner using a 30 s DBS-OFF/ON cycling paradigm, as illustrated in FIG. 8. Patients in both phases underwent multiple fMRI sessions with DBS-ON at the four electrode contacts while maintaining voltage, frequency, and pulse-width constant. Optimal clinical DBS parameters for patients in the retrospective phase were defined a priori by a movement disorder neurologist according to previously published algorithms. The order of non-optimal contact stimulation was randomized. During fMRI, only the left DBS electrode was turned ON. Following MRI, the motor component of the Unified Parkinson's Disease Rating Scale (UPDRS-III) was obtained at each contact. DBS electrode position and volume of tissue activated (VTA) were estimated to confirm stimulation of the target structure.

Figure 9B:
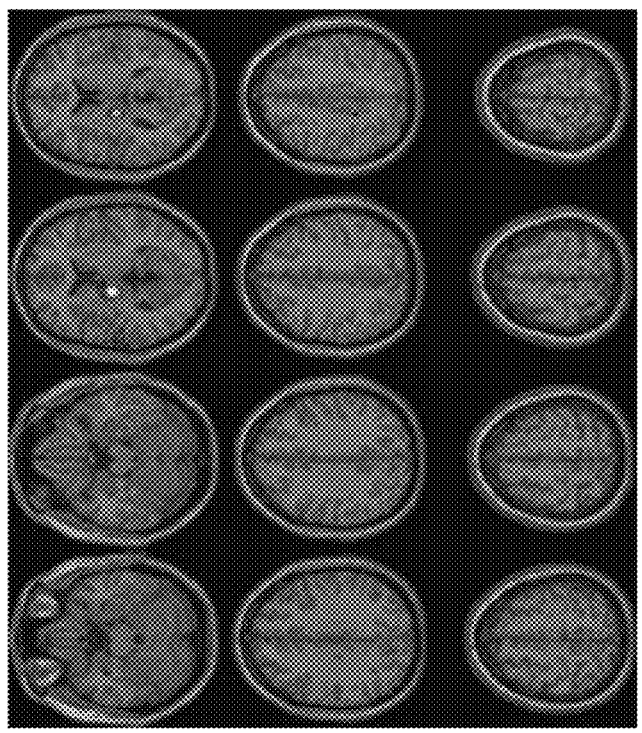
FIG. 9B illustrates fMRI brain patterns across the cohort of patients in the retrospective phase, for non-optimal DBS contacts, identified using group-level analysis.
Figure 9A:
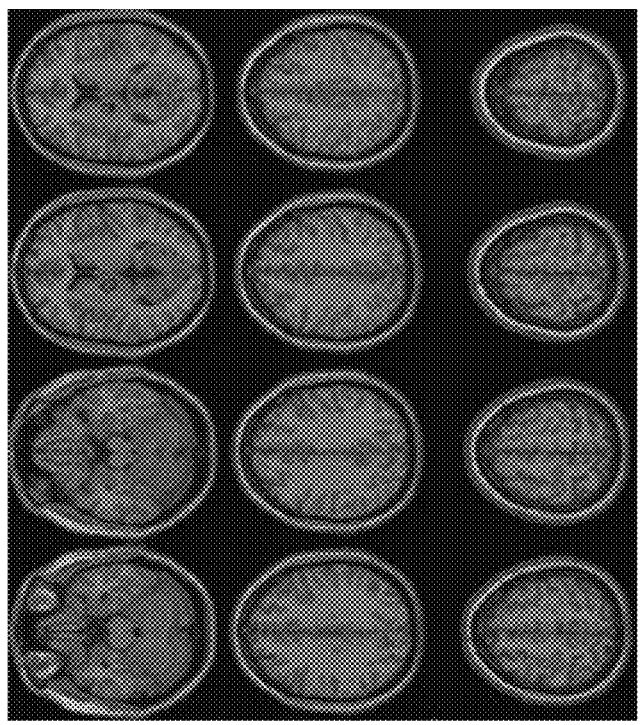
FIG. 9A illustrates fMRI brain patterns across the cohort of patients in the retrospective phase, for optimal DBS contacts, identified using group-level analysis.
Figures 10A, 10B:
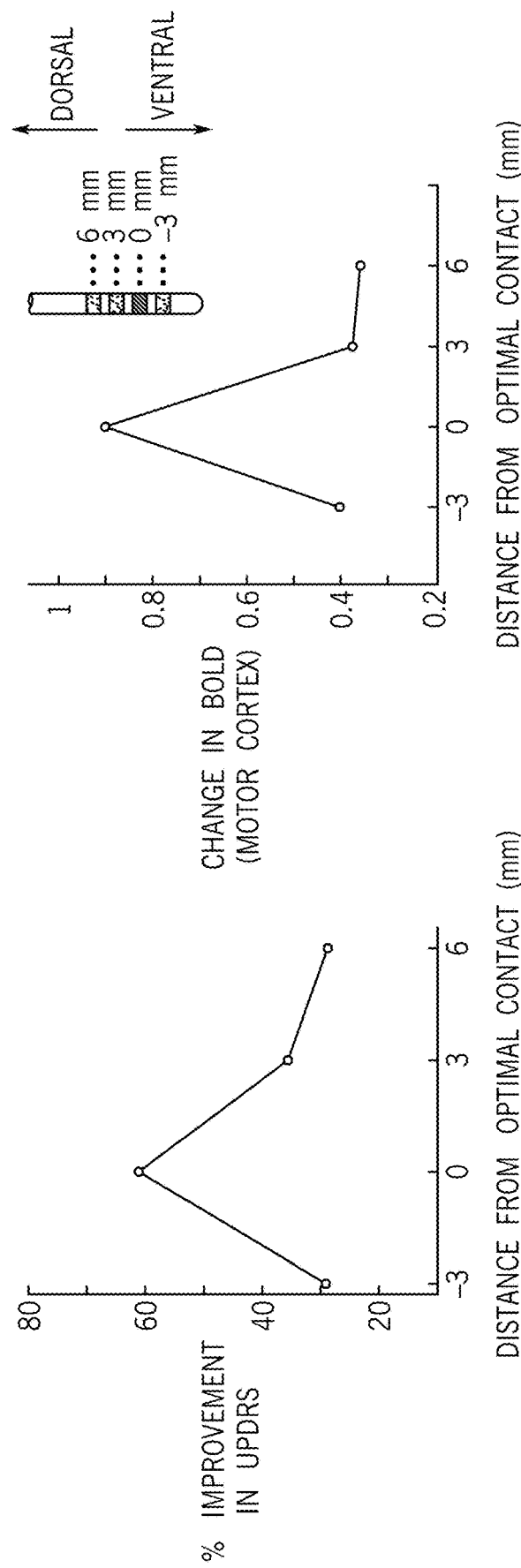
FIG. 10A illustrates UPDRS improvement in a patient from the prospective phase for optimal and non-optimal DBS contacts.
FIG. 10B illustrates a normalized BOLD response in a patient from the prospective phase for optimal and non-optimal DBS contacts.
Figures 11A, 11B:
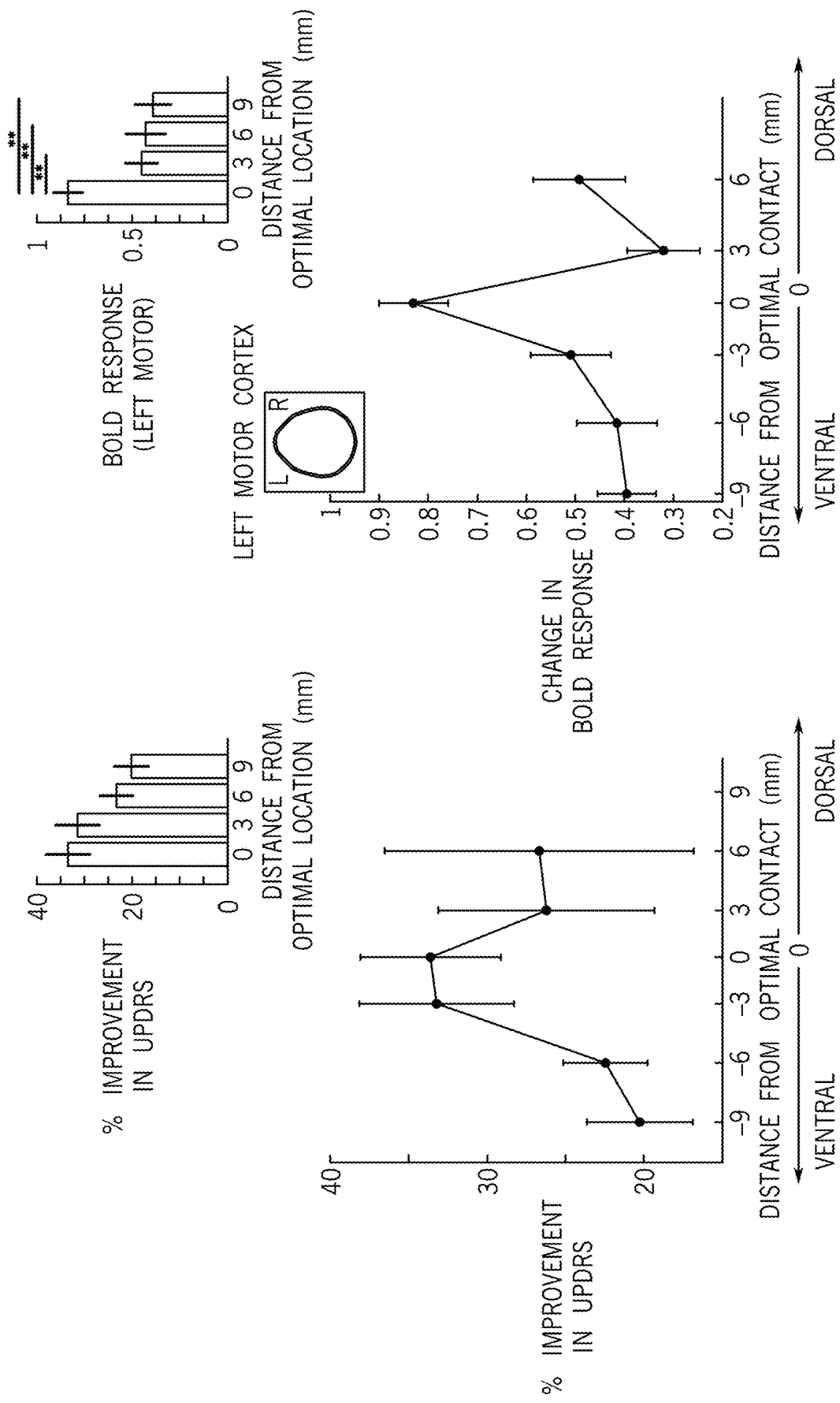
FIG. 11A illustrates UPDRS improvement in patients from the retrospective phase for optimal and non-optimal DBS contacts.
FIG. 11B illustrates a normalized BOLD response in patients from the retrospective phase for optimal and non-optimal DBS contacts.

For patients with a priori clinically optimized settings in the first phase, fMRI responses from the patients were analyzed to (1) define a pattern of fMRI response corresponding to optimal clinical benefits and (2) build a machine learning (ML) model to predict the optimal contact location. Statistical parametric maps were estimated for each subject using a 30 s DBS-ON/OFF block design in SPM12. Group-level analyses were performed to identify fMRI brain patterns across patients, as shown in FIGS. 9A-9B, while BOLD and UPDRS changes as a function of distance from the optimal contact are shown FIGS. 10A-10B and 11A-11B. Statistical metrics of functional activation were extracted from sixteen regions-of-interest (ROIs) to build a predictive ML model that classified the optimal contact using linear discriminant analysis (LDA).

Four patients undergoing early DBS programming were included in the second phase. Each patient's fMRI responses were fed to the ML model created with the retrospective data to prospectively predict the optimal DBS target. The ML model accurately predicted the clinically optimal contacts in the patients undergoing early programming, so as to allow for prediction of DBS parameters to be used to achieve an optimal therapeutic effect in the patient.

Example 2

The example described below refers to treatment of patients suffering from Parkinson's disease (PD) in the subthalamic nucleus (STN) and deemed a candidate for DBS therapy, with DBS electrodes implanted in either the STN or globus pallidus internal (GPI). As stated above, embodiments of the invention are directed to a system and method for predicting a set or combination of DBS parameters that provide an optimal therapeutic effect in the patient—i.e., optimal DBS parameters. In the example illustrated here below, the frequency of the DBS signal was cycled, while the voltage, pulse-width, and active electrode contact remained constant; however, as described above, it is recognized that exemplary embodiments of the invention are directed to methods where a sweep of one or more of the voltage, frequency, pulse-width, and contact used are performed—i.e., a sweep across a multi-dimensional parameter space of DBS parameters.

In performing a method to output this prediction, the method was performed on a total of 11 subjects. After a T1-weighted anatomical acquisition, all patients were set on a 30 s DBS ON/30 s DBS OFF cycling paradigm. fMRI was acquired on a 1.5 T MR scanner for 6-minutes using whole brain GE-EPI. fMRI cycling and stimulation were synchronized using a synchronization box. Each patient underwent one scan at their clinically optimized settings (including optimal frequency) and 2-4 scans at clinically non-optimal frequency settings (60-220 Hz). fMRI data were slice time corrected, motion corrected, rigid registered to T1-weighted image, non-rigid registered to Montreal Neurological Institute atlas, and spatially smoothed. Functional activation maps (t-maps) were estimated using 30 s ON/OFF block design at a voxel level. Response maps were thresholded at $p<0.05$ for visualization.

Figure 12C:
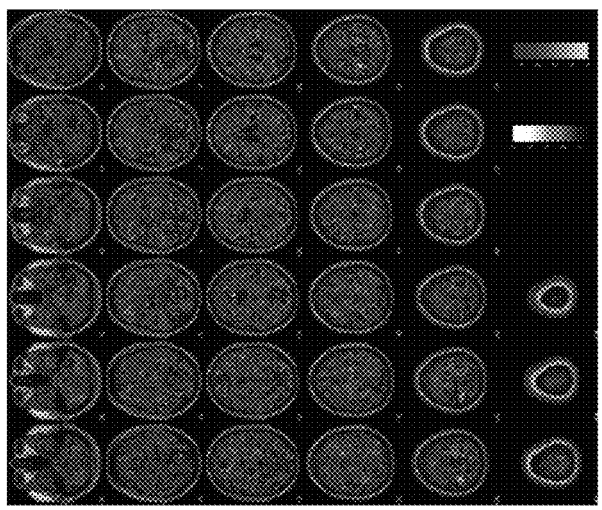
FIG. 12C illustrates a comparison of the motor cortex at optimal vs. non-optimal DBS frequency settings.
Figure 12B:
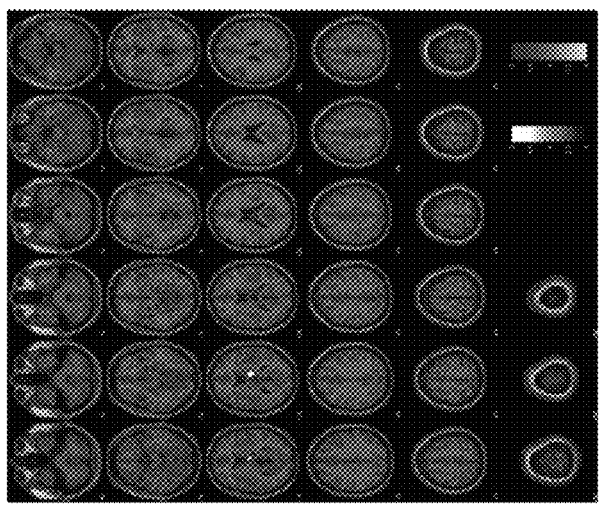
FIG. 12B illustrates bilateral thalamic activation and deactivation in the right motor cortex for non-optimal DBS frequency settings.
Figure 12A:
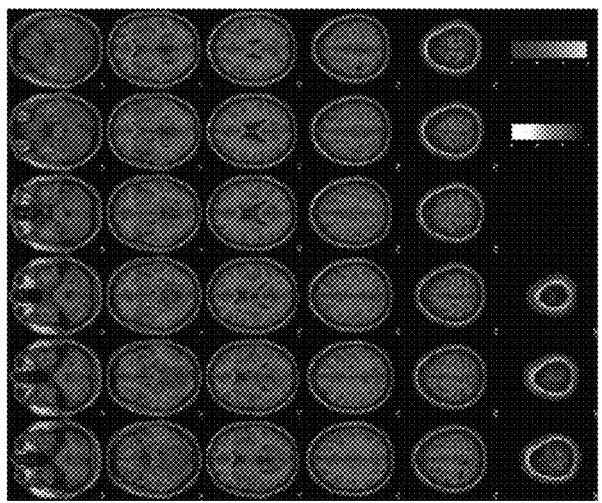
FIG. 12A illustrates activation in the motor cortex and posterior cerebellum, and deactivation in secondary visual and inferior frontal cortices for an optimal DBS frequency setting.

The fMRI response maps were different for optimal and non-optimal frequency settings (FIG. 1). Group-level analysis for all patients at an optimal frequency settings showed activation in the bilateral thalamus, motor cortex, and posterior cerebellum, and showed deactivation in secondary visual and inferior frontal cortices (FIG. 12A). In contrast, the non-optimal frequency settings showed deactivation in the right motor cortex (FIG. 12B). Across subjects, the motor cortex showed significantly greater activation in optimal compared to non-optimal frequency settings FIG. 12C).

Figure 13B:
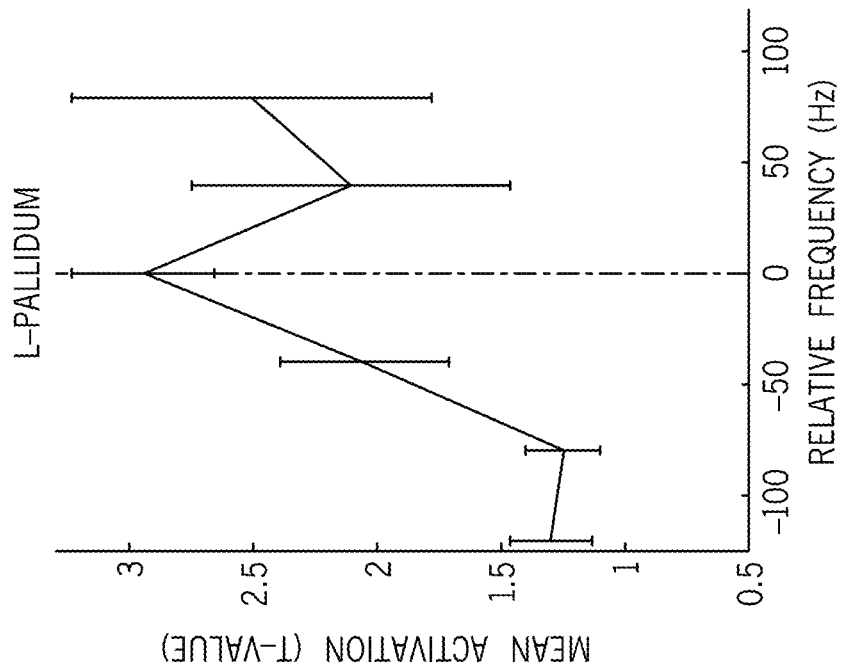
FIG. 13A-F illustrate comparisons of activation and deactivation in various regions/structures of the brain for optimal vs. non-optimal DBS frequency settings.
Figure 13A:
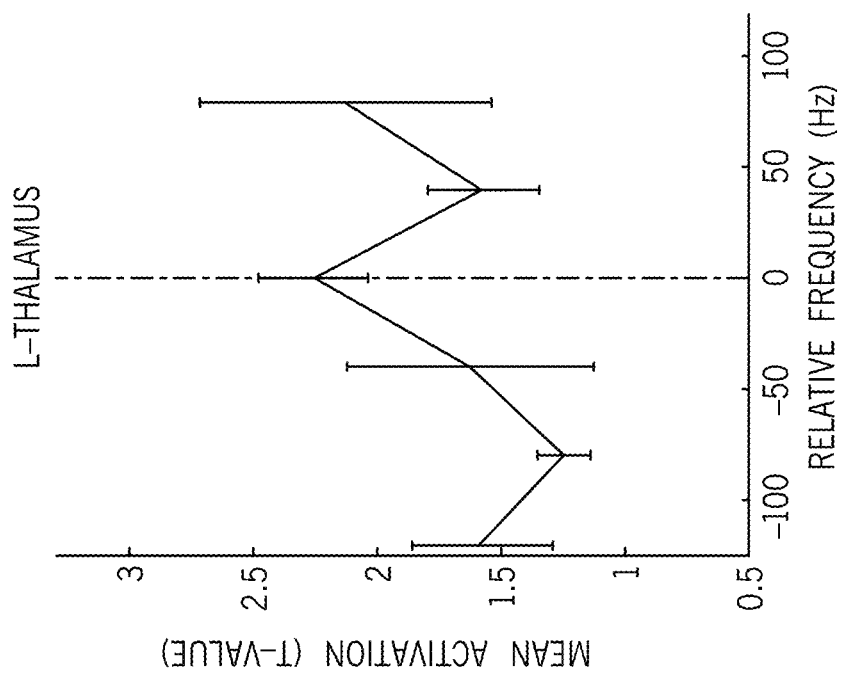
Figure 13D:
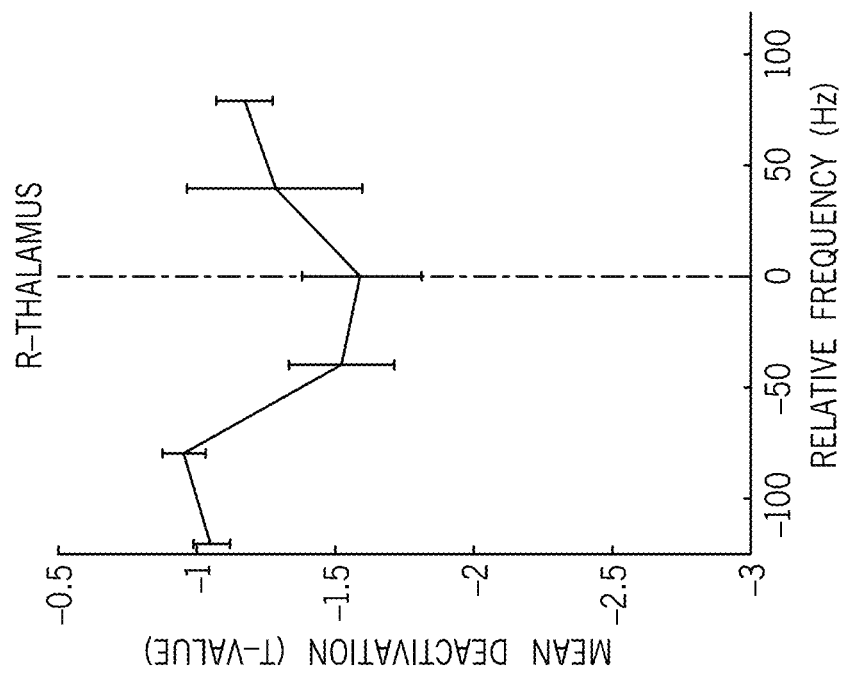
Figure 13C:
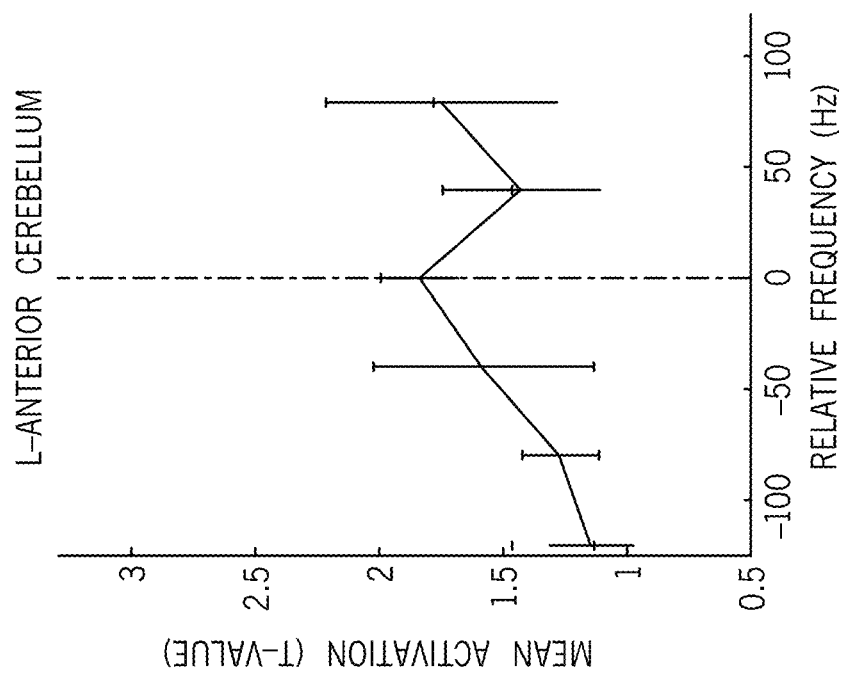
Figure 13F:
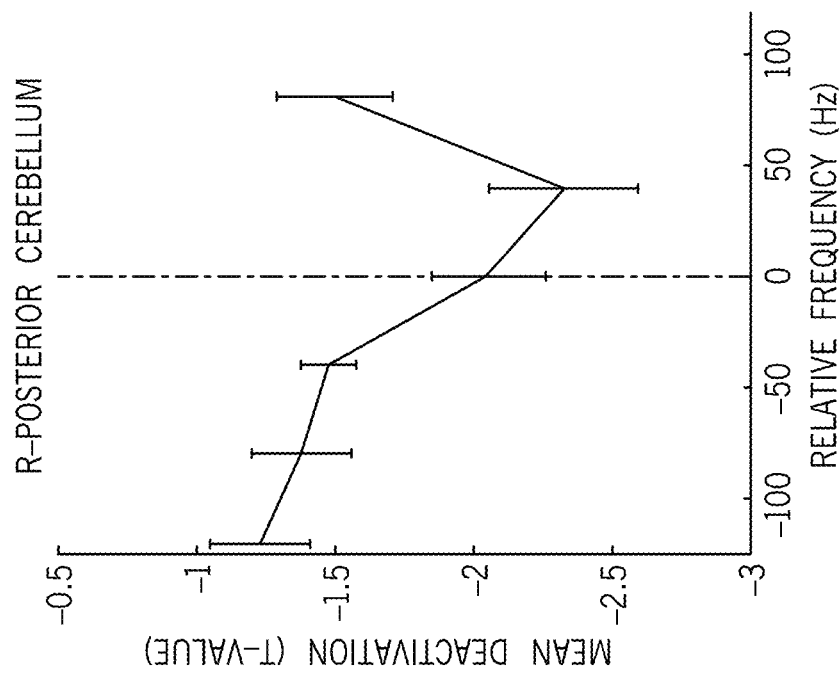
Figure 13E:
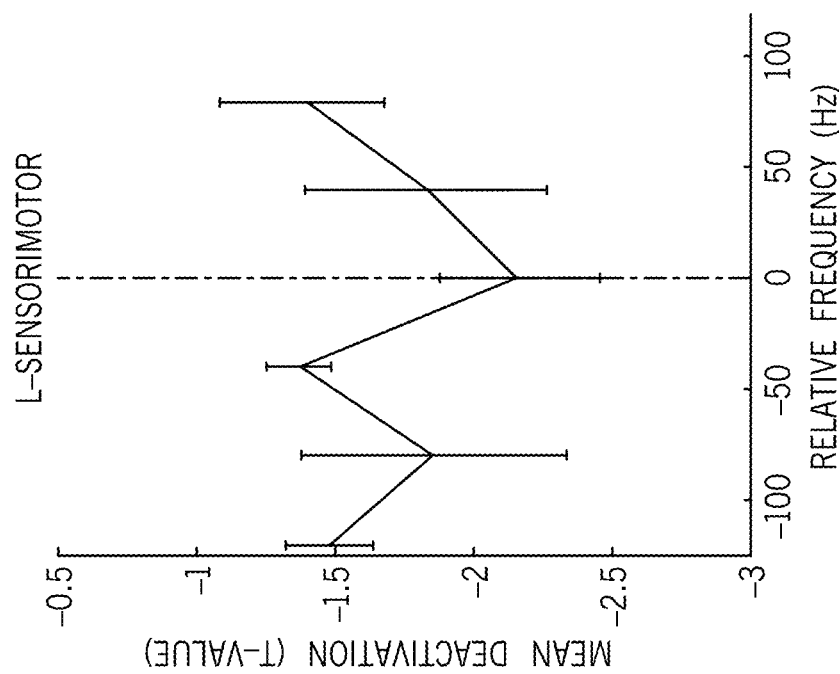

Mean t-values were calculated for 16 ROIs including the thalamus, pallidum, sensorimotor cortex, anterior and posterior cerebellum, primary and secondary visual areas and operculum. While optimal frequencies in the cohort ranged from [60-220 Hz] in order to enable group-level analysis, each patient's frequencies were mapped to a scale relative to the optimal frequency, which was set to 0 (FIGS. 13A-13F). Thalamus, pallidum and anterior cerebellar regions showed significantly stronger activation in optimal compared to non-optimal frequencies (FIGS. 13A-13C). Sensorimotor cortex and posterior cerebellum showed significantly stronger deactivation for optimal compared to non-optimal frequencies (FIGS. 13D-13F).

Beneficially, embodiments of the invention thus provide a system and method for optimizing DBS parameters (one or more of voltage, frequency, contact, and pulse-width) for a patient or prospective patient in an automated manner. The system and method use both connectivity and statistical brain network mapping to predict optimal voltage, frequency, contact, and pulse-width for each patient, providing a comprehensive solution for optimizing DBS excitation parameters. The method for DBS parameter optimization is not limited to post-operative scans, but may be performed using imaging data pre-surgically, without DBS electrode implantation, to provide a determination of whether the patient is a suitable candidate for DBS treatment and, if so, to enable identification of optimal DBS parameters for treatment of that patient. Still further, the system and method for optimizing DBS parameters enable such optimization in a single session, rather than in a 3-6 month timeframe as is typical for this optimization A technical contribution for the disclosed method and apparatus is that it provides for a computer implemented system and method for optimizing one or more DBS parameters in an automated fashion.

Therefore, according to one embodiment of the invention, a system for predicting optimal DBS parameters for a patient includes a DBS system controlled to send each of a plurality of DBS signals to one or more electrodes surgically implanted within one or more regions of a patient brain, wherein in sending the plurality of DBS signals the DBS system is controlled to perform a sweep of one or more DBS parameters, with each of the plurality of DBS signals comprising a different combination of DBS parameters. The system also includes a brain response acquisition system synchronized with the DBS system and controlled to collect brain response data resulting from each of the plurality of DBS signals. The system further includes a prediction system operably connected to the brain response acquisition system, the prediction system comprising a processor programmed to extract statistical metrics of brain response in the patient brain from the brain response data, access a DBS functional atlas comprising brain response maps derived from DBS treatment at optimal DBS parameter settings for a plurality of diseases, and predict optimal DBS parameters for the patient based on the statistical metrics of brain response and the DBS functional atlas.

According to another embodiment of the invention, a system for predicting optimal DBS parameters applied by one or more DBS electrodes for treatment of a patient includes a brain response acquisition system controlled to collect functional brain data from the patient in a resting state and a prediction system operably connected to the brain response acquisition system. The prediction system includes a processor programmed to estimate a functional connectome of the patient from the functional brain data, access a functional brain atlas comprising brain response maps for one or more disease-specific regions-of-interest (ROIs) or voxels, extract disease-specific graph theoretic metrics for one or more ROIs in the functional connectome using the functional brain atlas, and predict optimal DBS parameters for the patient using the disease-specific graph theoretic metrics.

According to yet another embodiment of the invention, a method for optimizing parameters of a DBS pulse signal applied by a DBS electrode for treatment of a patient includes inputting functional brain data into a predictor system, the functional brain data acquired responsive to a sweeping across one or more DBS parameters of a multi-dimensional parameter space of DBS parameters. The method also includes extracting statistical metrics of brain response from the functional brain data for one or more ROIs or voxels of the brain via the predictor system, accessing a DBS functional atlas comprising brain response maps derived from DBS treatment at optimal DBS parameter settings for a plurality of diseases via the predictor system, and predicting optimal DBS parameters for the patient based on the statistical metrics of brain response and the DBS functional atlas via the predictor system.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for predicting optimal deep brain stimulation (DBS) parameters for a patient, the system comprising:
    a DBS system controlled to send each of a plurality of DBS signals to one or more electrodes surgically implanted within one or more regions of a patient brain, wherein in sending the plurality of DBS signals the DBS system is controlled to perform a sweep of one or more DBS parameters, with each of the plurality of DBS signals comprising a different combination of DBS parameters;
    a brain response acquisition system synchronized with the DBS system and controlled to collect brain response data resulting from each of the plurality of DBS signals; and
    a prediction system operably connected to the brain response acquisition system, the prediction system comprising a processor programmed to:
        extract statistical metrics of brain response in the patient brain from the brain response data;
        access a DBS functional atlas comprising brain response maps derived from DBS treatment at optimal DBS parameter settings for a plurality of diseases; and
        predict optimal DBS parameters for the patient based on the statistical metrics of brain response and the DBS functional atlas.

2. The system of claim 1 wherein the one or more DBS parameters swept by the DBS system and the optimal DBS parameters predicted by the prediction system comprise one or more of signal voltage and an activated contact selected from a plurality of contacts on each of the one or more electrodes.

3. The system of claim 1 wherein, in sweeping the one or more DBS parameters, the DBS system is controlled such that an order in which the DBS signals comprising the combinations of DBS parameters used for the stimulations is randomized.

4. The system of claim 1 wherein the processor is further programmed to preprocess the brain response data to remove artifacts and prepare the brain response data for subsequent analysis and processing.

5. The system of claim 1 wherein sequences of brain response data are collected using a 30 second DBS signal On/Off cycling paradigm or through a continuous firing of the DBS signal.

6. The system of claim 1 wherein, in extracting statistical metrics of brain response, the processor is programmed to determine activation and deactivation in one or more regions-of-interest (ROIs) or voxels of the brain.

7. The system of claim 6 wherein the processor is programmed to extract features from the brain response maps for the one or more ROIs or voxels using the statistical metrics of brain response, so as to obtain a normalized ROI or voxel response.

8. The system of claim 7 wherein, in predicting the optimal DBS parameters, the processor is programmed to input the extracted features into a machine learning algorithm stored thereon, the machine learning algorithm derived from the DBS functional atlas.

9. The system of claim 1 wherein the DBS functional atlas further comprises brain response maps from hundreds or thousands of patients acquired responsive to application of optimal and non-optimal DBS parameter combinations, from which brain response maps correlated with optimal DBS parameters are identified for disease-specific ROIs or voxels.

10. The system of claim 1 further comprising a synchronization box configured to synchronize collection of the brain response data with application of the plurality of DBS signals to the one or more electrodes.

11. The system of claim 1 wherein the brain response acquisition system comprises a magnetic resonance imaging (MRI) apparatus configured to acquire MRI data of the brain, the MRI data acquired pre-operatively or post-operatively.

12. The system of claim 1 wherein the processor is further programmed to input the optimal DBS parameters to the DBS system so as to cause the one or more electrodes to apply DBS signals having the optimal DBS parameters to the patient.

13. The system of claim 1 wherein, in predicting the optimal DBS parameters, the processor is programmed to rank different combinations of optimal DBS parameters.

14. A system for predicting optimal deep brain stimulation (DBS) parameters applied by one or more DBS electrodes for treatment of a patient, the system comprising:
   a brain response acquisition system controlled to collect functional brain data from the patient in a resting state; and
   a prediction system operably connected to the brain response acquisition system, the prediction system comprising a processor programmed to:
      estimate a functional connectome of the patient from the functional brain data;
      access a functional brain atlas comprising brain response maps for one or more disease-specific regions-of-interest (ROIs) or voxels;
      extract disease-specific graph theoretic metrics for one or more ROIs in the functional connectome using the functional brain atlas; and
      predict optimal DBS parameters for the patient using the disease-specific graph theoretic metrics.

15. The system of claim 14 wherein the predicted optimal DBS parameters comprise one or more of signal voltage and an activated contact selected from a plurality of contacts on each of the one or more DBS electrodes.

16. The system of claim 14 wherein the functional brain atlas comprising the brain response maps are derived from resting state functional brain data obtained prior to a DBS implantation surgery and from brain responses resulting from DBS treatment at optimal DBS parameter settings for a plurality of diseases, post DBS implantation surgery.

17. The system of claim 14 wherein, in predicting the optimal DBS parameters, the processor is programmed to input the disease-specific graph theoretic metrics into a machine learning algorithm stored thereon, the machine learning algorithm derived from the functional brain atlas.

18. The system of claim 17 wherein the brain response acquisition system comprises a magnetic resonance imaging (MRI) apparatus configured to acquire MRI data of the brain.

19. A method for predicting optimal parameters of a DBS pulse signal applied by a DBS electrode for treatment of a patient, the method comprising:
   inputting functional brain data into a predictor system, the functional brain data acquired responsive to a sweeping across one or more DBS parameters of a multi-dimensional parameter space of DBS parameters;
   extracting statistical metrics of brain response from the functional brain data for one or more regions-of-interest (ROIs) or voxels of the brain via the predictor system;
   accessing a DBS functional atlas comprising brain response maps derived from DBS treatment at optimal DBS parameter settings for a plurality of diseases via the predictor system; and
   predicting one or more optimal DBS parameters for the patient based on the statistical metrics of brain response and the DBS functional atlas via the predictor system.

20. The method of claim 19 wherein predicting the one or more optimal DBS parameters comprises predicting one or more of a signal voltage and an activated contact of a plurality of contacts on the DBS electrode.

21. The method of claim 19 further comprising extracting features from the brain response maps for the one or more ROIs or voxels using the statistical metrics and the DBS functional atlas via the predictor system.

22. The method of claim 19 further comprising inputting the extracted features into a machine learning algorithm programmed in the predictor system, the machine learning algorithm derived from the DBS functional atlas.

23. The method of claim 19 wherein the DBS functional atlas comprises brain response maps from hundreds or thousands of patients acquired responsive to application of optimal and non-optimal DBS parameter combinations, from which brain response maps correlated with optimal DBS parameters are identified for disease-specific ROIs or voxels.

24. The method of claim 19 further comprising outputting the optimal DBS parameters from the predictor system to a DBS system, so as to cause one or more electrodes of the DBS system to apply DBS signals having the optimal DBS parameters to the patient.

* * * * *